United States Patent [19]

Rattner

[11] Patent Number: 4,901,709

[45] Date of Patent: Feb. 20, 1990

[54] SHOCK WAVE SOURCE

[75] Inventor: Manfred Rattner, Buckenhof, Fed. Rep. of Germany

[73] Assignee: Siemens Aktiengesellschaft, Berlin and Munich, Fed. Rep. of Germany

[21] Appl. No.: 214,048

[22] Filed: Jun. 30, 1988

[30] Foreign Application Priority Data

Jul. 8, 1987 [DE] Fed. Rep. of Germany ... 8709363[U]

[51] Int. Cl.[4] .............................................. A61B 17/22

[52] U.S. Cl. .................................. 128/24 A; 367/175; 606/128

[58] Field of Search ............. 128/24 A, 328; 367/141, 367/142, 175, 182; 181/142, 402

[56] References Cited

U.S. PATENT DOCUMENTS 4,674,505 6/1987 Pavli et al. .
4,793,329 12/1988 Mahler et al. .................... 128/24 A

FOREIGN PATENT DOCUMENTS 0095383 11/1983 European Pat. Off. .
0133946 3/1985 European Pat. Off. .
0209053 1/1987 European Pat. Off. .
704633 2/1954 United Kingdom .

*Primary Examiner*—Ruth S. Smith
*Attorney, Agent, or Firm*—Hill, Van Santen, Steadman & Simpson

[57] ABSTRACT

A shock wave source for use in a shock wave generator in an apparatus for extracorporeal lithotripsy treatment of a patient has a shock wave tube filled with a shock wave propagating medium with one end closed by a flexible sack for coupling to the patient, and an opposite end closed by a membrane having at least a portion thereof which is electrically conductive, and a coil disposed adjacent the membrane and connected to a high voltage pulse source. When high voltage pulses are applied to the coil, an electromagnetic field is generated which rapidly repells the membrane, thereby generating a shock wave. The membrane has a flexible base covered by a number of discrete laminae of conductive material. At least some of the laminae may have respectively different mass moments of inertia and/or electrical conductivity. The shock wave source is suitable for treating calculi such as kidney stones.

8 Claims, 4 Drawing Sheets

SHOCK WAVE SOURCE

BACKGROUND OF THE INVENTION

1. Field of the Invention

The present invention is directed to a shock wave source of the type suitable for treating calculi in the body of a patient, and in particular to a shock wave source operating on the principle of rapid electromagnetic repulsion of a membrane to generate shock waves.

2. Description of the Prior Art

Shock wave sources are known in the art which generally include a shock wave tube filled with a shock wave propagating medium, such as water, with one end of the tube being closed by a flexible sack which can be pressed against the patient, and an opposite end closed by an electrically conductive membrane. The membrane is disposed opposite a coil, and is separated therefrom by an insulating layer. The coil is connected to a supply which generates high voltage pulses.

A shock wave source of this type permits the generation of focused shock waves, which can be directed to a calculus to be disintegrated, for example a kidney stone, the action of the shock waves on the calculus pulverizing the calculus to such an extent that the particles can be naturally eliminated. Shock wave generation occurs by the application of a high voltage pulse to the coil, which may be a spiral winding, so that an electromagnetic field is generated which causes the membrane to be rapidly repelled, thereby generating a pressure pulse which is converted by a focusing means into a shock wave, which is directed to the calculus.

SUMMARY OF THE INVENTION

It is an object of the present invention to provide a membrane for use in a shock wave source of the type described above which permits a shock wave following a favorable path to the calculus to be generated.

The above object is achieved in accordance with the principles of the present invention in a shock wave source having a membrane consisting of a flexible base, which is covered by a plurality of laminae, each laminae consisting of electrically conductive material. The laminae are discrete, i.e., are spaced from each other on the flexible base. Each individual laminae on the membrane is repelled by the electromagnetic field generated by the coil. The propagation of the generated shock wave is thus significantly faster at the edge region of the membrane, in comparison to a conventional membrane having a uniform conductive layer thereon. A shock wave source which is optimally constructed for generating a selected shock wave following a selected path in a embodiment of the invention wherein the laminae, or at least some of the laminae, exhibit respectively different mass moments of inertia and/or different electrical conductivity. The desired shock wave path can be achieved by a suitable selection of the different mass moments of inertia and/or the conductivity.

The membrane may be planar or curved. A suitable focusing of the shock waves can be achieved without the need for an acoustic lens by suitable curving the membrane.

DESCRIPTION OF THE PREFERRED EMBODIMENTS

Figure 1:
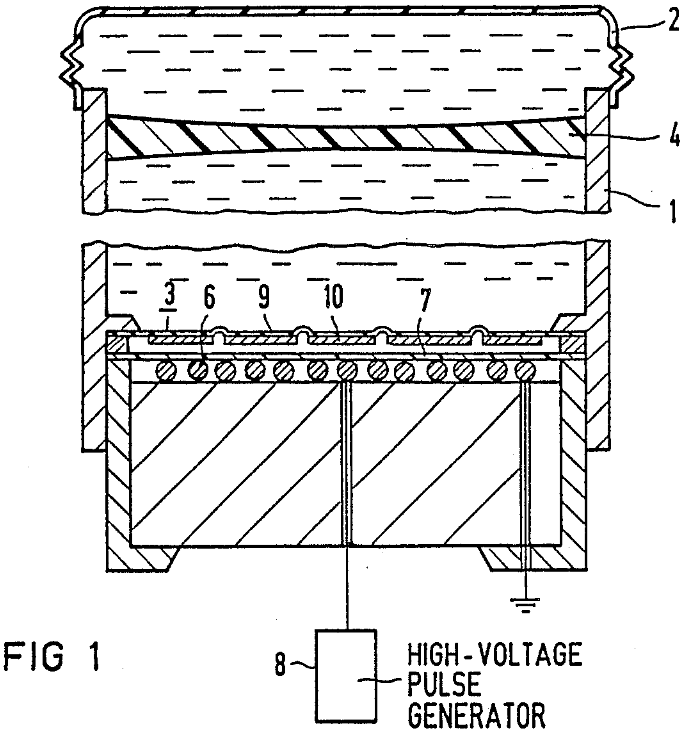
FIG. 1 is a side sectional view of a shock wave source constructed in accordance with the principles of the present invention.

A shock wave source constructed in accordance with the principles of the present invention is shown in FIG. 1, and includes a shock wave tube having a side for application to a patient closed by a flexible sack 2. The flexible sack 2 can be placed against a patient. The opposite end of the shock wave tube 1 is closed by a membrane 3. The volume defined by the tube 1, the sack 2 and the membrane 3 is filled with a liquid coupling agent, such as water. An acoustic lens 4 for focusing generated shock waves is also disposed within the tube 1.

Generating of a shock wave is achieved by means of a flat coil 6, disposed opposite the membrane 3. The flat coil 6 is in the form of a spiral, and is separated from the membrane 3 by an insulator layer 7. The flat coil 6 has one terminal connected to ground, and another terminal connected to a high voltage pulse generator 8.

Figure 2:
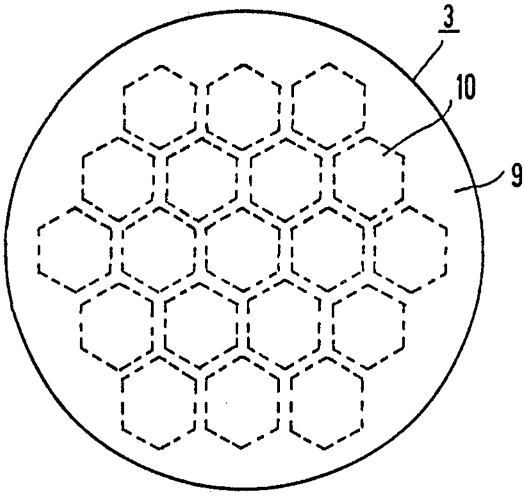
FIG. 2 is a plan view of one embodiment of the membrane used in the shock wave source of FIG. 1.

As shown in both FIGS. 1 and 2, the membrane 3 consists of a flexible base 9, for example a rubber foil, which is covered by a plurality of laminae 10, each of the laminae 10 consisting of electrically conductive material. In the embodiment of FIGS. 1 and 2, the laminae 10 are hexagonal, thus achieving a high surface coverage. It is also possible to use other geodesic shapes for the laminae 10 which also achieve high surface coverage, for example, rectangles or squares.

When the high voltage pulse from the generator 8 is supplied to the flat coil 6, due to the eddy currents generated in the laminae 10, the membrane 3 will be rapidly repelled by the electromagnetic field generated by the flat coil 6. A pressure pulse is then generated in the coupling agent within the shock wave tube 1, and is focused by the acoustic lens 4 to a calculus to be disintegrated in a patient. By the use of the plurality of laminae 10, a favorable shock wave path is achieved, in particular a rapid shock wave generation at the edge region of the membrane 3 is achieved. The desired shock wave course can be selected by suitable selection of the respective mass moments of inertia and/or the electrical conductivity of the individual laminae 10.

Figure 3:
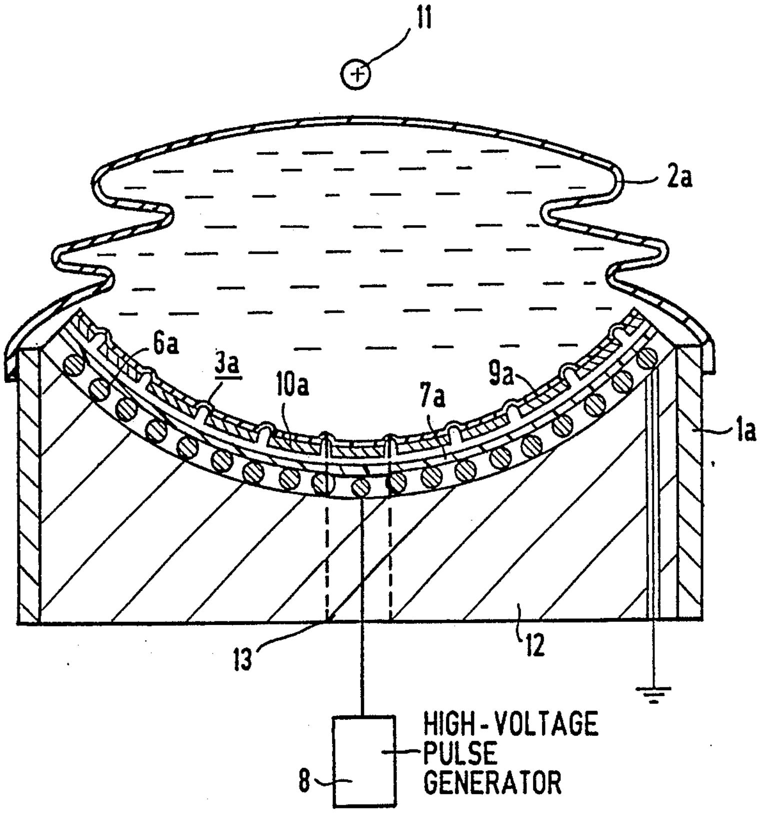
FIG. 3 is a side sectional view of a shock wave source constructed in accordance with the principles of the present invention in a further embodiment.

In an embodiment of the invention shown in FIG. 3, a membrane 3a is curved around a region 11, which is a focus for the membrane 3a. The membrane 3a has an inside surface covered by laminae 10a consisting of electrically conductive material and having suitable respective mass moments of inertia. The coil 6a, like the membrane 3a and the insulator layer 7a, is curved around the region 11. An acoustic lens is not needed in the liquid-filled space between the sack 2a and the membrane 3a, because focusing is achieved by the curvature of the membrane 3a, the coil 6a, the insulator 7a and the flexible base 9a. A coil carrier 12 is provided, which may have a central opening 13 therein for receiving an ultrasound probe to identify the position of the calculus to be disintegrated.

Figure 4:
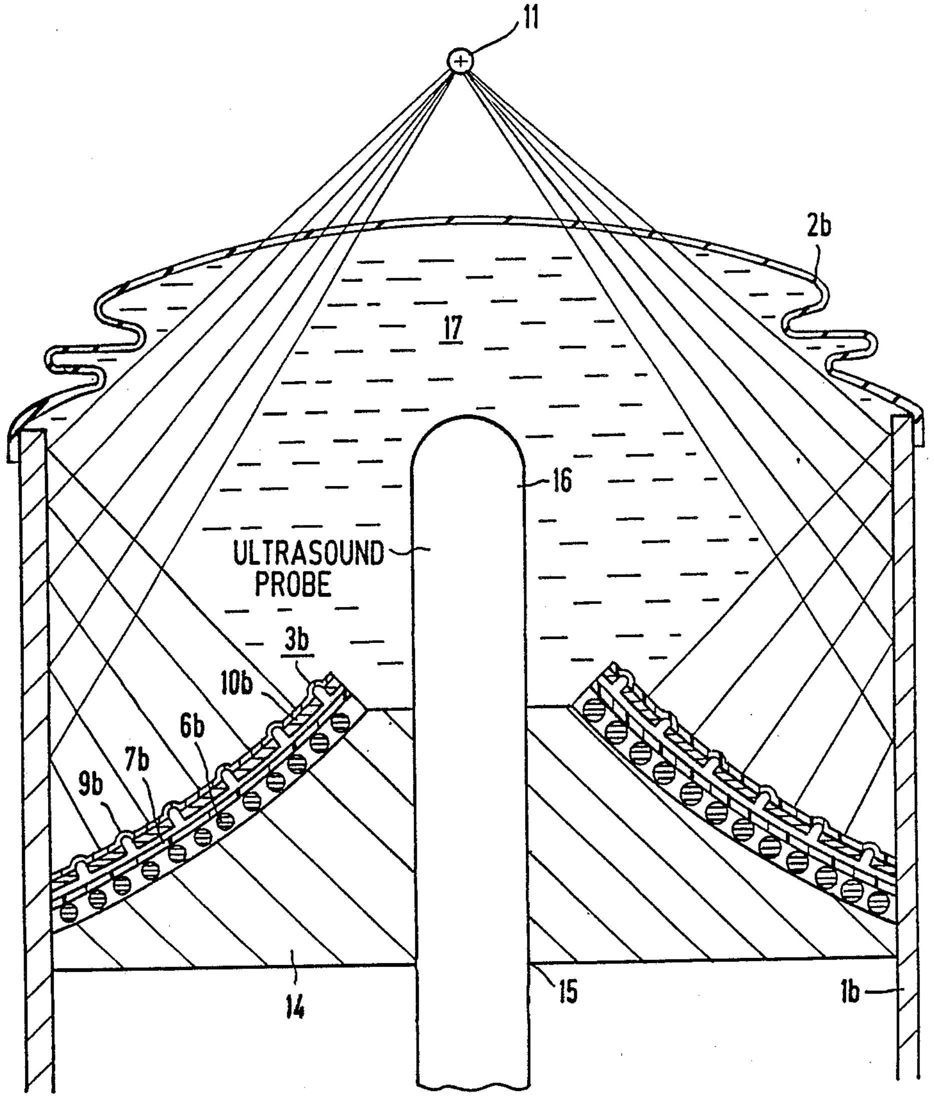
FIGS. 4 and 5 are side sectional views of further embodiments of shock wave sources constructed in accordance with the principles of the present invention having an ultrasound probe disposed therein.

In the embodiment of FIG. 4, a membrane 3b is provided in the tube 1b terminated by the sack 2b, the membrane 3b being curved in the direction toward the inside of the shock wave tube 1b. Shock waves generated by the laminae 10b are thus directed against the inside wall of the tube 1b, and are reflected to the region of focus 11. A relatively large volume 17, which is free of shock waves, is thus achieved, and an ultrasound probe 16 can be introduced. In this embodiment, the carrier 14 for the coil 6b has a central opening 15 therein, which receives the ultrasound probe 16. An insulator layer 7b is again provided, and the membrane 3b again consists of a flexible base 9b covered by the laminae 10b.

The embodiment of FIG. 3 achieves a relatively short approach path for higher-frequency shock waves, whereas the embodiment of FIG. 4 provides a relatively long approach path through the propagating medium.

Figure 5:
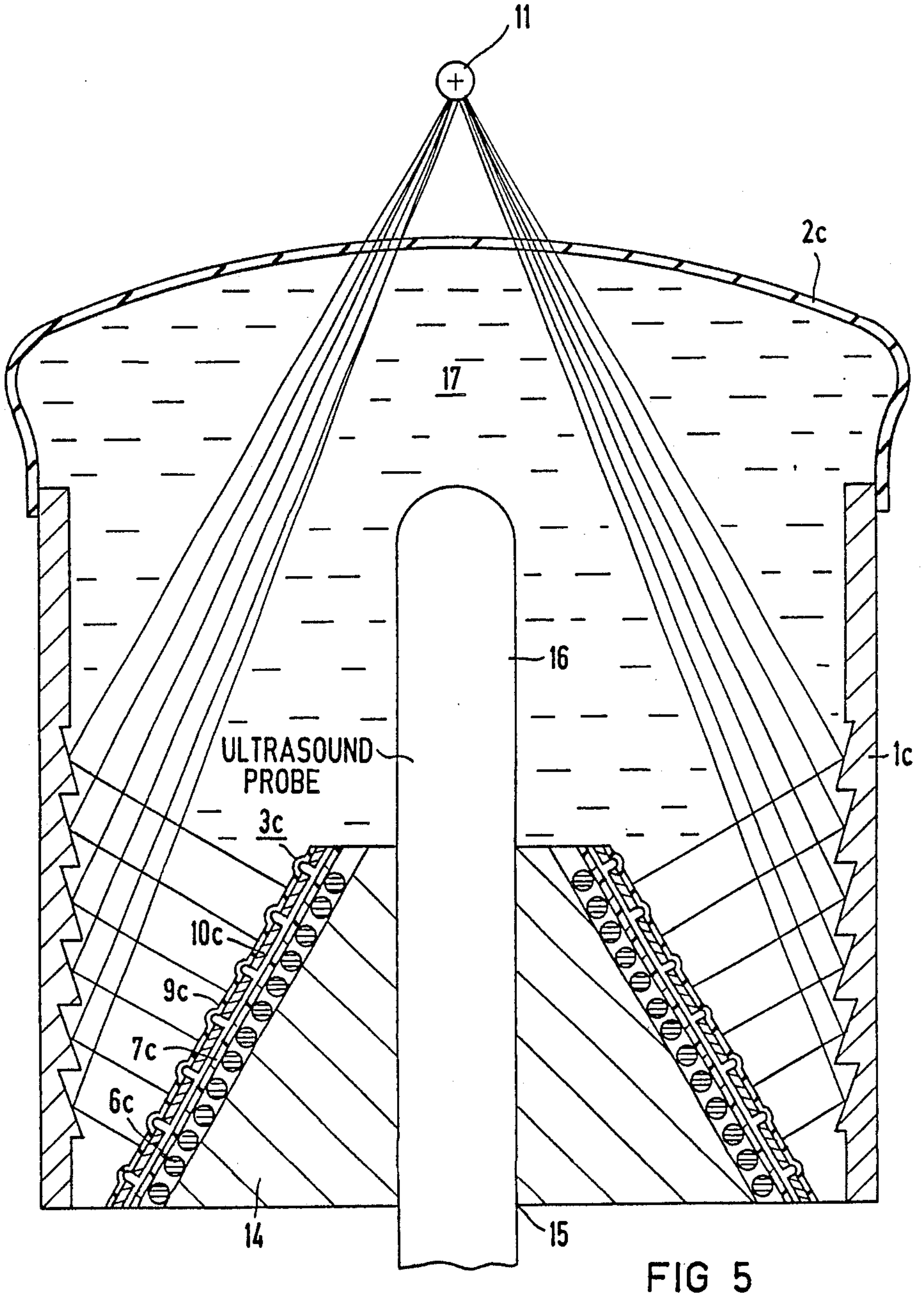

In the embodiment of FIG. 5, the shock wave source is formed by a membrane 3c having a flexible base 9c with laminae 10c thereon, a coil 6c and an insulator 7c, all of which are in the form of a truncated cone. The shock wave tube 1c has an inside surface which is stepped so that a plurality of stepped reflectors are formed for focusing the shock waves to the region of focus 11.

In all of the embodiments, the laminae can be vulcanized to the flexible base, or may be glued thereto or laminated thereon.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave source for extracorporeal lithotripsy treatment of calculi in a patient, said shock wave source comprising:
- a housing containing a volume filled with a shock wave conducting medium closed at one end by a flexible cover adapted for application against said patient; means for generating high-voltage pulses;
- a coil connected to said means for generating high-voltage pulses;
- an insulator layer disposed adjacent said coil;
- a membrane closing an opposite end of said housing and disposed adjacent said insulator layer, said membrane consisting of a flexible base covered by a plurality of discrete geodesic laminae consisting of electrically conductive material, whereby upon the supply of a high-voltage pulse to said coil by said means for generating high-voltage pulses, said coil generates an electromagnetic field which rapidly repells said membrane to generate a pressure pulse and;
- means for focusing said pressure pulse into a shock wave on said calculus.

2. A shock wave source as claimed in claim 1, wherein at least some of said laminae have respectively different mass moments of inertia.

3. A shock wave source as claimed in claim 1, wherein at least some of said laminae have respectively different electrical conductivity.

4. A shock wave source as claimed in claim 1, wherein at least some of said laminae have respectively different mass moment of inertia and at least some of said laminae have respectively different electrical conductivity.

5. A shock wave source as claimed in claim 1, wherein said means for focusing is an acoustic lens disposed between said membrane and said flexible cover.

6. A shock wave source as claimed in claim 1, wherein said means for focusing is a carrier for said coil, said insulator layer and said membrane which curves said membrane around a focus.

7. A shock wave source as claimed in claim 1 wherein said housing comprises a cylindrical shock wave tube having an interior wall, and wherein said means for focusing is a carrier for said coil, said insulator layer and said membrane which curves said membrane toward said interior wall of said tube so that said pressure pulses are reflected off of said interior wall toward a focus.

8. A shock wave source as claimed in claim 1, wherein said housing comprises a cylindrical shock wave tube having an interior wall, and wherein said means for focusing is a carrier for said coil, said insulator layer and said membrane being in the form of a truncated cone, and a plurality of steps on said interior wall of said tube, so that said pressure pulses from said membranes are reflected by said steps on said interior wall toward a focus.

* * * * *